United States Patent [19]

Askew

[11] Patent Number: 5,718,865
[45] Date of Patent: Feb. 17, 1998

[54] MOULDABLE ALUM COMPOSITION

[76] Inventor: Darren John Askew, Unit 11, Northcliffe Terrace, Surfers Paradise, Queensland 4217, Australia

[21] Appl. No.: 750,748
[22] PCT Filed: Jun. 29, 1995
[86] PCT No.: PCT/AU95/00384
§ 371 Date: Dec. 24, 1996
§ 102(e) Date: Dec. 24, 1996
[87] PCT Pub. No.: WO96/00566
PCT Pub. Date: Jan. 11, 1996

[30] Foreign Application Priority Data

Jun. 29, 1994 [AU] Australia .................. PM6529

[51] Int. Cl.$^6$ ........................................... C08J 5/00
[52] U.S. Cl. ................. 264/331.11; 264/239; 264/299; 264/331.11; 424/409; 424/497; 419/61; 419/63; 419/65; 419/66
[58] Field of Search ................. 264/239, 299, 264/331.11; 424/409, 497; 419/61, 63, 65, 66

[56] References Cited

FOREIGN PATENT DOCUMENTS

| 0400546 | 12/1990 | European Pat. Off. . |
| 0448278 | 9/1991 | European Pat. Off. . |
| 0454127 | 10/1991 | European Pat. Off. . |
| WO94/13255 | 6/1994 | WIPO . |
| WO94/28866 | 12/1994 | WIPO . |

*Primary Examiner*—Samuel A. Acquah
*Attorney, Agent, or Firm*—Hoffman, Wasson & Gitler

[57] ABSTRACT

A moulded alum composition is formed by mixing crushed solid alum with a polyol plasticiser followed by heating to form a slurry, and then pouring the mixture into a mould. No mechanical cutting and grinding is required and weakening cracks and fissures present in the raw alum are removed.

9 Claims, No Drawings

MOULDABLE ALUM COMPOSITION

THIS INVENTION relates to a mouldable composition and particularly to a mouldable alum composition.

BACKGROUND ART

Alum is an inorganic compound and generally contains two metals, two sulphate groups and water. A compound of this type is called a hydrated double salt. Alums are hydrated double salts that have similar compositions and similar crystalline structures.

Alums have a variety of uses. For instance, alums have been used in the dyeing industry, for water purification, for paper sizing, for fire-proofing fabrics, in fire extinguishers, and in medicinal and cosmetic fields.

It is the medicinal and cosmetic field where alums have particular interest. For instance, potassium alum has astringent properties, and is used in medicine to treat certain skin conditions, to reduce excessive perspiration, and to stop bleeding from small cuts. Dilute solutions (1–4%) have been used as mouth washes and gargles. Solutions of 5–10% are used to harden the skin, especially of the feet. Powdered forms of alum, or strong aqueous solutions of alum, are used as styptic for minor cuts and abrasions. Compositions containing talc and alum have been used as foot powders. Recent applications of alum containing solutions include bladder irrigations, and for the control of bladder haemorrhaging.

Commercially, the two most important alums are potassium alum and ammonium alum. Ammonium alum is manufactured by crystallisation from an aqueous solution of ammonium sulphate and aluminium sulphate. Ammonium alum crystals are also produced by treating a mixture of aluminium sulphate and sulphuric acid with ammonia.

Potassium alum occurs naturally in the minerals alunite and kalinite, but can also be artificially manufactured by treating aluminium oxide with sulphuric acid and potassium sulphate. Another method of production involves heating of alunite followed by treatment with sulphuric acid to obtain crystals of the alum.

It is known that alums, and especially potassium alum and ammonium alum, can be used as solid crystalline deodorants, especially for under-arm use.

For solid deodorant use, it is necessary to manufacture the alum into a stick-like shape having rounded corners and no sharp or abrasive edges or portions.

Currently, the only method available to make such an alum deodorant stick is by cutting and grinding raw alum lumps, which is labour-intensive and also places limitations on the shape and size of the products.

Currently, crystalline lumps of the alum (which can be naturally-occurring alunite, or kalinite, or artificially manufactured crystals), are cut into sections by mechanical cutting devices and then core-drilled to produce a solid cylinder of alum. The cylinder has flat top and bottom ends and a cylindrical side wall and is used as a deodorant stick.

The method of cutting and core drilling results in a large amount of waste product which can not be used as deodorant sticks. Also, the cylinder has a flat top wall which results in a fairly sharp edge between the top wall and the side wall. Some manufacturers further shape the stick by mechanically grinding the cylinder of alum to provide a rounded top portion which is then smoother to use.

Another disadvantage with the naturally-occurring or artificially made alums is that they have numerous cracks and fissures throughout them. This makes mechanical cutting and core drilling difficult and results in many accidental breakages with subsequent discarding of the product. Also, consumers generally do not like the cracks and fissures which detracts from the appearance of the deodorant stick. The cracks and fissures also reduce the strength of the deodorant stick making it susceptible to breakage if dropped or handled roughly, or during the packaging and transportation of the product to the retail outlets.

Attempts have made to shape alums into deodorant sicks or other shapes without requiring mechanical cutting, grinding or other shaping techniques. For instance, alum such as the dodecahydrate form of potassium alum has a melting point of 92.5° C. However, it is found that melting the alum followed by re-solidification transforms the alum into a weak and crumbly structure making it useless as a commercial deodorant stick. While not wishing to be bound by theory, it appears that when the alum is melted, the hygroscopic nature results in the weakening of the alum structure upon re-solidification and exposure to air.

OBJECT OF THE INVENTION

The present invention is directed to a method by which an alum can be moulded thereby doing away with, or reducing, the need for mechanical cutting or grinding, and where the moulded alum has sufficient strength make it useful as a deodorant stick, or useful for other applications.

In one form, the invention results in a method of producing a shaped alum containing composition, the method comprising
1) granulating an alum composition of Formula 1,

$$M1\ M2\ (XO4)2.YH_2O$$

wherein
M1 is a positive univalent ion;
M2 is a positive trivalent ion;
X is sulphur or selenium; and
Y is a number between 0–30.
2) Mixing the product of Step 1 with a plasticiser to form a mouldable product,
3) moulding the mixture of Step 2 into a desired shape.

Optionally, the mixture of Step 2 can be heated to promote conversion of the mixture to the mouldable product. It is preferred that the mixture is in the form of a slurry.

Preferably M1 is selected from the group consisting of sodium, potassium, rubidium, caesium, ammonium, thallium, silver, hydrazine, hydroxylamine, organic amines and lithium.

Preferably M2 is selected from the group consisting of aluminium, iron, chromium, manganese, indium, gallium, iridium, titanium, vanadium, cobalt and rhodium.

Preferably Y is 12.

Preferred components are potassium alum $KAl(SO4)_2.12H_2O$ and ammonium alum $NH_4\ Al(SO4)_2.12H_2O$.

Other alums may include caesium alum, iron alum, chrome alum, and chromoselenic alum.

The plasticiser may be a liquid plasticiser or a plasticiser which is in a liquid or substantially liquid form during the mixing step. Preferably a liquid plasticiser is used.

The liquid plasticiser may comprise an organic polyol. The organic polyol may be a linear polyol having between $C_2$–$C_{10}$ carbons. Suitable such polyols can include glycerol, and/or sorbitol ($C_6H_{14}O_6$). Other plasticisers and solvents may also be used.

Preferably, the plasticiser is one which is stable during the mixing and moulding steps, and therefore glycerol is a preferred plasticiser. If other plasticisers are used may discolour during the mixing and any heating step, such a plasticiser may still be acceptable depending on the end use of the moulded product. If the discolouration is to be masked or converted, it is possible to add dyes, colorants and the like to the mixture.

The amount of plasticiser used can vary depending on the type of plasticiser, the type of alum, and the end use of the moulded product. The end use may require consideration of hardness, durability, and lasting properties. A plasticiser ratio of between 0.1 to 50% by weight of the alum can be used. If the plasticiser is glycerol, and the alum is potassium alum or ammonium alum, approximately 0.5 to 15% by weight, or by volume of glycerol, can be used.

During the method of preparing the product, various additives can be used. These additives may include fragrances, perfumes, borax, conditioners, natural oils, and medicinal compounds such as antiseptic agents. It may be necessary to adjust the process parameters such as mixing times and heating and select the additives depending on their properties such as boiling point, stability, and the like. Such a choice would be apparent to a person skilled in the art.

The mixing of the plasticiser with the granulated alum composition may be achieved manually, mechanically, automatically, semi-automatically, or by other means.

Similarly, the moulding of the mixture to a desired shape can be done by pouring, pumping or pressing the mixture into a mould or by other means.

BEST MODE

Example 1

Potassium alum is crushed into a particle size approximating that of sugar granules, that is, typically between 0.1 to 3 millimetre diameter granules. The crushed potassium alum is added to a mixing device (many types of mixing devices can be used) and 0.5% to 15% by weight or volume of glycerin is added. The mixture is mixed and heated to between 100° to 110° C. during or after which it forms a mouldable slurry. The slurry is poured into moulds which are cylindrical and have a domed bottom wall. When cooled, the mould is removed to provide a deodorant stick which can be about 16 centimetres long, 5 centimetres in diameter, with a small taper from a wider base to a narrower domed top. The base of the stick can be wrapped to allow it to be touched and can be used as a solid deodorant stick.

Example 2

Potassium alum is crushed in a manner similar to Example 1. Between 0.5 to 15% by weight or volume of glycerin is added to the mixture. The mixture is mixed and heated until water displaced from the alum begins to boil. At this boiling, or substantially at the boiling point, additives such as borax or fragrances can be added. The mixture is then cooled and rehydrated by addition of water, and the cooled rehydrated mixture is poured into moulds to form desired shapes, such as deodorant sticks, and the like.

Example 3

1000 g of potassium alum is crushed as per example 1 and is added to a plastic container. 20 g of glycerin is added to the container. The container containing the mixture is subjected to microwave heating (700 watt output) for 9 minutes. At this stage sufficient heating and water displacement has occurred. The heated mixture is removed from the microwave source and is stirred for 10–15 seconds to ensure mixing of the contents. The mixture is then poured into a mould and allowed to cool before being removed from the mould.

Example 2 illustrates that borax can be mixed in to the slurry to form a useful product. As glycerol is unstable at higher temperatures, the heating to boiling point is kept to a minimum time before cooling occurs. Also, any additives that are added at the elevated temperature must be such that do not immediately boil away or decompose.

It can be seen that the above method will allow alum, such as potassium alum and ammonium alum, to be moulded to any desired shape and does not require extensive cutting or grinding. There is little or no wastage as any off-cuts can be simply ground and added to the mixture.

An advantage of the moulding step is that any fissures and cracks are closed to provide a stronger and more visually appealing product. The plasticiser overcomes the previous disadvantage of crumbling which occurs when the alums are heated and cooled by themselves. While not wishing to be bound by theory, it appears that polyol plasticisers may hydrogen bond with, or become included with, the alum structure.

The method creates an uniformly perfect product every time without the problems of cracking or crumbling. The moulding method facilitates mass production with little or no wastage, and does not have any significant limitation to size or shape.

If glycerine is used as the plasticiser, a further advantage is that glycerine is an accepted skin conditioner. Thus, the moulded alum is less harsh on the skin than cut and shaped alum deodorants which have a high acidity factor and can result in skin rashes occurring on some people.

The addition of borax in Example 2 reduces the acidity of the alum to allow the deodorant stick to be used on the most sensitive skin types.

The deodorant need not contain currently used ingredients such as aluminium chlorohydrate, which appears to have detrimental qualities.

By being able to add plasticisers and also other additives, fragrances, skin conditioning agents, and the like can be moulded entirely through and into the alum, whereas currently cut and shaped alums can only coat the outside of the stick with such additives.

It should be appreciated that various other changes and modifications can be made to the embodiments described. For instance, the moulded alum can be used other than for deodorants. It can be used to provide relief of tinea, dermatitis, cold sores, acne, shaving rash, cuts and skin irritations.

I claim:

1. A method of producing a shaped alum containing composition, comprising the steps of:

granulating an alum composition of a Formula, $$M1\ M2\ (XO4)2.YH_2O$$

wherein

M1 is a positive univalent ion;

M2 is a positive trivalent ion;

X is sulphur or selenium; and

Y is a number between 0–30; and

Mixing between 85–99.5% of said granulated alum composition with between 0.5–15% by weight or volume of a plasticizer to form a mouldable product.

2. The method of producing a shaped alum containing composition of claim 1, further comprising the step of mouldir said mouldable product into a desired shape.

3. The method of producing a shaped alum containing composition of claim 1, wherein M1 is selected from the group consisting of sodium, potassium, rubidium, caesium, ammonium, thallium, silver, hydrazine, hydroxylamine, organic amines and lithium.

4. The method of producing a shaped alum containing composition of claim 1, wherein M2 is selected from the group consisting of aluminum, iron, chromium, manganese, indium gallium, iridium, titanium, vanadium, cobalt and rhodium.

5. The method of producing a shaped alum containing composition of claim 1, wherein said alum composition is selected from the group consisting of a potassium alum and an ammonium alum.

6. The method of producing a shaped alum containing composition of claim 1, wherein said plasticizer is an organic polyol.

7. The method of producing a shaped alum containing composition of claim 6, wherein said organic polyol is a linear polyol having between 2–6 carbon atoms.

8. The method of producing a shaped alum containing composition of claim 1, wherein said plasticizer is selected from the group consisting of glycerol and sorbitol.

9. A method of producing a shaped alum containing composition comprising granulating an alum selected from potassium alum or an ammonium alum to a particle size of about 0.1 mm to 5 mm, adding between 0.1–15% by weight or by volume of a glycerol, mixing said alum and said glycerol together to form a mixture, heating said mixture to about 100°–110° C. to form a slurry, pouring said slurry into a mould, cooling said slurry and removing said slurry from said mould to form a shaped alum composition.

* * * * *